(12) United States Patent
Breininger et al.

(10) Patent No.: US 11,229,773 B2
(45) Date of Patent: Jan. 25, 2022

(54) DETERMINING A VESSEL PUNCTURE POSITION

(71) Applicant: Siemens Healthcare GmbH, Erlangen (DE)

(72) Inventors: Katharina Breininger, Erlangen (DE); Marcus Pfister, Bubenreuth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 582 days.

(21) Appl. No.: 16/169,097

(22) Filed: Oct. 24, 2018

(65) Prior Publication Data
US 2019/0126008 A1 May 2, 2019

(30) Foreign Application Priority Data
Oct. 27, 2017 (EP) .................................... 17199026

(51) Int. Cl.
*A61B 5/00* (2006.01)
*A61M 25/01* (2006.01)
(Continued)

(52) U.S. Cl.
CPC ......... *A61M 25/0105* (2013.01); *A61B 6/504* (2013.01); *G06T 7/11* (2017.01);
(Continued)

(58) Field of Classification Search
CPC ........ A61M 25/0105; A61M 2205/502; A61M 2025/0166; A61M 2205/3327; G06T 7/70;
(Continued)

(56) References Cited

U.S. PATENT DOCUMENTS

| 8,929,631 B2 | 1/2015 | Pfister et al. |
| 2009/0016483 A1 | 1/2009 | Kawasaki et al. |

(Continued)

FOREIGN PATENT DOCUMENTS

| CN | 102172330 A | 9/2011 |
| CN | 103340602 A | 10/2013 |

(Continued)

OTHER PUBLICATIONS

Bangalore Sripal et al. "Femoral Arterial Access and Closure" in: Circulation, vol. 124, Issue 5, pp. e147-e156, Aug. 2, 2011, DOI: 10.1161/CIRCULATIONAHA.111.032235.
(Continued)

*Primary Examiner* — Joel Lamprecht
(74) *Attorney, Agent, or Firm* — Harness, Dickey & Pierce, P.L.C.

(57) ABSTRACT

A method is for determining a vessel puncture position including reception of a first image dataset of a region of interest via an interface, the first image dataset mapping the vessel. The method further includes determination of a vessel line of the vessel based on the first image dataset via a computing unit. The method further includes determination of a gradient measure based on the vessel line. Finally, the method includes a determination of the vessel puncture position based on the gradient measure. A position-determining unit, a computer program product and a computer-readable storage medium are for determining a vessel puncture position.

27 Claims, 7 Drawing Sheets

(51) Int. Cl.
*G06T 7/70* (2017.01)
*G06T 7/11* (2017.01)
*A61B 6/00* (2006.01)
*A61B 6/12* (2006.01)

(52) U.S. Cl.
CPC .............. *G06T 7/70* (2017.01); *A61B 5/0035* (2013.01); *A61B 5/489* (2013.01); *A61B 6/12* (2013.01); *A61M 2025/0166* (2013.01); *A61M 2205/3327* (2013.01); *A61M 2205/502* (2013.01)

(58) Field of Classification Search
CPC ........... G06T 7/11; A61B 6/504; A61B 5/489; A61B 5/0035; A61B 6/12
See application file for complete search history.

(56) References Cited

U.S. PATENT DOCUMENTS

| | | | |
|---|---|---|---|
| 2011/0235876 A1 | 9/2011 | Pfister et al. | |
| 2015/0094567 A1 | 4/2015 | Pfister | |
| 2017/0245822 A1 | 8/2017 | Vaillant et al. | |
| 2018/0000441 A1* | 1/2018 | Wang | G06T 5/30 |

FOREIGN PATENT DOCUMENTS

| | | |
|---|---|---|
| CN | 106780527 A | 5/2017 |
| CN | 107041729 A | 8/2017 |
| CN | 107126227 A | 9/2017 |
| DE | 102012205647 A1 | 10/2013 |
| DE | 102013205647 A1 | 10/2014 |
| DE | 102015202287 A1 | 8/2016 |
| EP | 3384846 A1 | 10/2018 |

OTHER PUBLICATIONS

Chinese Office Action and English translation thereof dated Dec. 31, 2020.

Goel, Vikash Ravi et al. "Automated Vascular Geometric Analysis of Aortic Aneurysms" IEEE Computer Graphics and Applications, vol. 28, No. 3, pp. 76-86, 2008; DOI: 10.1109/MCG.2008.44 ; Electronic ISSN: 1558-1756.

Toth, Daniel et al. "Adaption of 3D Models to 2D X-Ray Images during Endovascular Abdominal Aneurysm Repair" MICCAI 2015: Medical Image Computing and Computer-Assisted Intervention, vol. 9349, Springer, Cham, pp. 339-346, 2015; DOI: https://doi.org/10.1007/978-3-319-24553-9_42 ; Online ISBN: 978-3-319-24553-9.

Lessard, Simon et al. "Automatic detection of selective arterial devices for advanced visualization during abdominal aortic aneurysm endovascular repair" Medical Engineering and Physics, vol. 37 No. 10, pp. 979-986, 2015; http://dx.doi.org/10.1016/j.medengphy.2015.07.007.

European Search Report for 17199026.0 dated Apr. 17, 2018.
Office Action for European Patent Application No. 17199026.0 dated May 7, 2021.

* cited by examiner

FIG 1
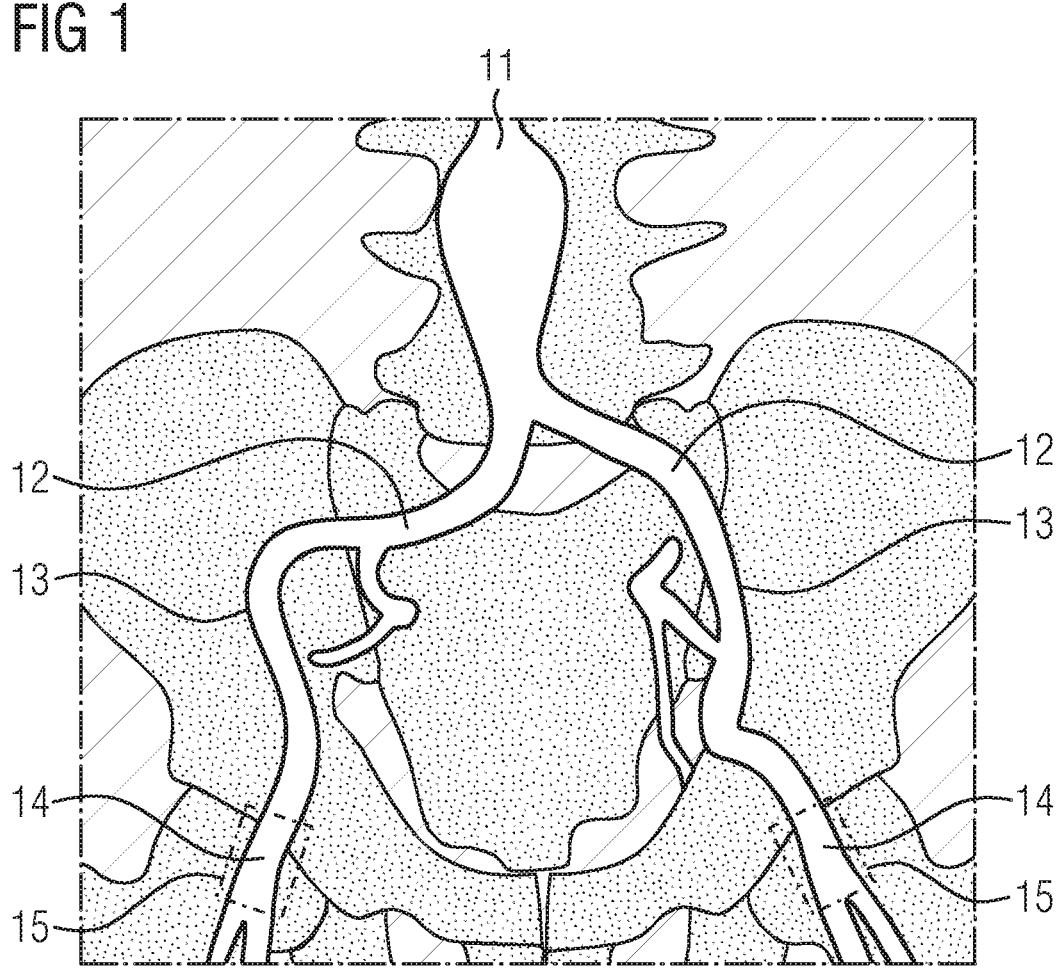
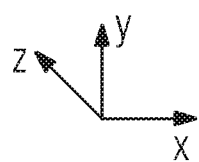

_US 11,229,773 B2_

DETERMINING A VESSEL PUNCTURE POSITION

PRIORITY STATEMENT

The present application hereby claims priority under 35 U.S.C. § 119 to European patent application number EP17199026.0 filed Oct. 27, 2017, the entire contents of which are hereby incorporated herein by reference.

FIELD

Embodiments of the invention generally relate to a method for determining a vessel puncture position.

BACKGROUND

To assist catheterization, it is known to depict previously recorded first image datasets together with second image datasets, wherein the second image datasets were recorded during the catheterization. Herein, it is in particular possible for the first image dataset to be recorded with a different modality than the second image dataset. For example, it is usual to combine computed tomography in advance of catheterization with X-ray projection via a C-arm X-ray machine during catheterization.

Superimposed depiction of first and second image datasets requires registration and is, for example, known from the U.S. Pat. No. 8,929,631 B2. However, if the catheter is extremely rigid, the vessel into which the catheter is introduced may be deformed and hence the superimposition of the first and the second image dataset is faulty (since, unlike the second image dataset, the first image dataset does not depict the shape of the vessel during catheterization).

Assuming that the catheter is located within the image, it is known from the publication US 20150094567 A1 to adapt the first image dataset based on the depiction of the catheter in the second image dataset. Furthermore, it is known from the publication EP 17164593.0, to include the rigidity of the catheter in this adaptation.

SUMMARY

Since a plurality of second image datasets are obtained during a catheter examination, it is usual for the image region of the second image datasets to be selected as small as possible in order to keep the radiation dose for the patient as low as possible. This implies that in particular the catheter is not depicted completely in the second image datasets. The inventors have recognized that outside the image region of the second image datasets, it is necessary to extrapolate the route of the catheter and this is associated with uncertainties.

At least one embodiment of the present invention provides additional information on the three-dimensional route of the catheter that enables more precise extrapolation of the route of the catheter.

Embodiments of the present invention are directed to a method for the determination of a puncture position; a position-determining unit; an imaging medical device; a computer program product; and a computer-readable storage medium.

Herein, the puncture position designates a point in a first image dataset describing the probable location at which the catheter penetrates a vessel. Since catheters can only be introduced at a few optimum locations, the puncture point can be determined entirely on the basis of the previously recorded first image data and does not need to be determined during catheterization. It is then possible to use this point in conjunction with the extrapolation of the route of the catheter as a fixed point for the adaptation of segmentation of the first image dataset.

Features, advantages or alternative embodiments mentioned herein should also be transferred to the other claimed subject matter and vice versa. In other words, the substantive claims (which are, for example, directed at a device) can also be developed with the features which are described or claimed in connection with a method. Herein, the corresponding functional features of the method are embodied by corresponding substantive modules.

At least one embodiment of the invention generally relates to a method for the determination of a vessel puncture position comprising the reception of a first image dataset of a region of interest via an interface, wherein the first image dataset maps the vessel. The vessel in particular passes through the region of interest. A further step of the method according to at least one embodiment of the invention is the determination of a vessel line of the vessel based on the first image dataset, via at least one processor. A further step of the method according to the invention is the determination of a gradient measure based on the vessel line. A further step of the method according to at least one embodiment of the invention is the determination of the vessel puncture position based on the gradient measure via the at least one processor.

At least one embodiment of the invention generally relates to a method for determining a vessel puncture position of a vessel, comprising:

receiving, via an interface, a first image dataset of a region of interest, the first image dataset mapping the vessel;

determining, via at least one processor, a vessel line of the vessel based on the first image dataset received;

determining, via the at least one processor, a gradient measure based on the vessel line determined; and determining, via the at least one processor, the vessel puncture position of the vessel based on the gradient measure determined.

At least one embodiment of the invention generally relates to a method for determining a vessel puncture position of a vessel, comprising:

receiving, via an interface, a first image dataset of a region of interest, the first image dataset mapping the vessel;

determining a projected vessel line by projection of the vessel line along a first direction, based on the first image dataset received;

determining a gradient measure based upon the projected vessel line determined, with respect to a second direction, the second direction being orthogonal to the first direction, and determining the vessel puncture position based on the gradient measure determined.

At least one embodiment of the invention also relates to a position-determining unit for the determination of a puncture position comprising:

an interface embodied to receive a first image dataset of a region of interest, wherein the first image dataset maps the vessel; and at least one processor, embodied to determine a vessel line of the vessel based on the first image dataset, determine a gradient measure based on the vessel line, and determine the vessel puncture position based on the gradient measure.

At least one embodiment of the invention also relates to a position-determining unit a position-determining unit for determining a puncture position of a vessel, comprising:

interface, embodied to receive a first image dataset of a region of interest, the first image dataset mapping the vessel; and at least one processor, embodied to determine a vessel line of the vessel based on the first image dataset received, determine a gradient measure based on the vessel line determined, and determine the vessel puncture position based on the gradient measure determined.

At least one embodiment of the invention also relates to a position-determining unit a position-determining unit for determining a puncture position of a vessel, comprising:

interface, embodied to receive a first image dataset of a region of interest, the first image dataset mapping the vessel; and at least one processor, embodied to determine a projected vessel line by projection of the vessel line along a first direction, based on the first image dataset received, determine a gradient measure based upon the projected vessel line determined, with respect to a second direction, the second direction being orthogonal to the first direction, and determine the vessel puncture position based on the gradient measure determined.

At least one embodiment of the invention furthermore relates to an imaging medical device comprising a position-determining unit according to at least one embodiment of the the invention. The imaging medical device is in particular embodied to record second image datasets. The imaging of the imaging medical device can in particular be based on ionizing radiation, in particular X-rays. The imaging medical device can in particular be a C-arm X-ray machine.

At least one embodiment of the invention also relates to a computer program product with a computer program and a computer-readable medium. A substantially software-based implementation has the advantage that it is also possible to retrofit position-determining units used to date in a simple way by way of a software update in order to operate in the manner according to at least one embodiment of the invention. In addition to the computer program, a computer program product of this kind can optionally include additional parts, such as, for example documentation and/or additional components and also hardware components, such as, for example, hardware keys (dongles etc.) for using the software.

BRIEF DESCRIPTION OF THE DRAWINGS

The following describes and explains the invention in more detail with reference to the example embodiments depicted in the figures.

FIG. 1 shows a schematic depiction of the pelvic region of a patient,

DETAILED DESCRIPTION OF THE EXAMPLE EMBODIMENTS

Figure 2:
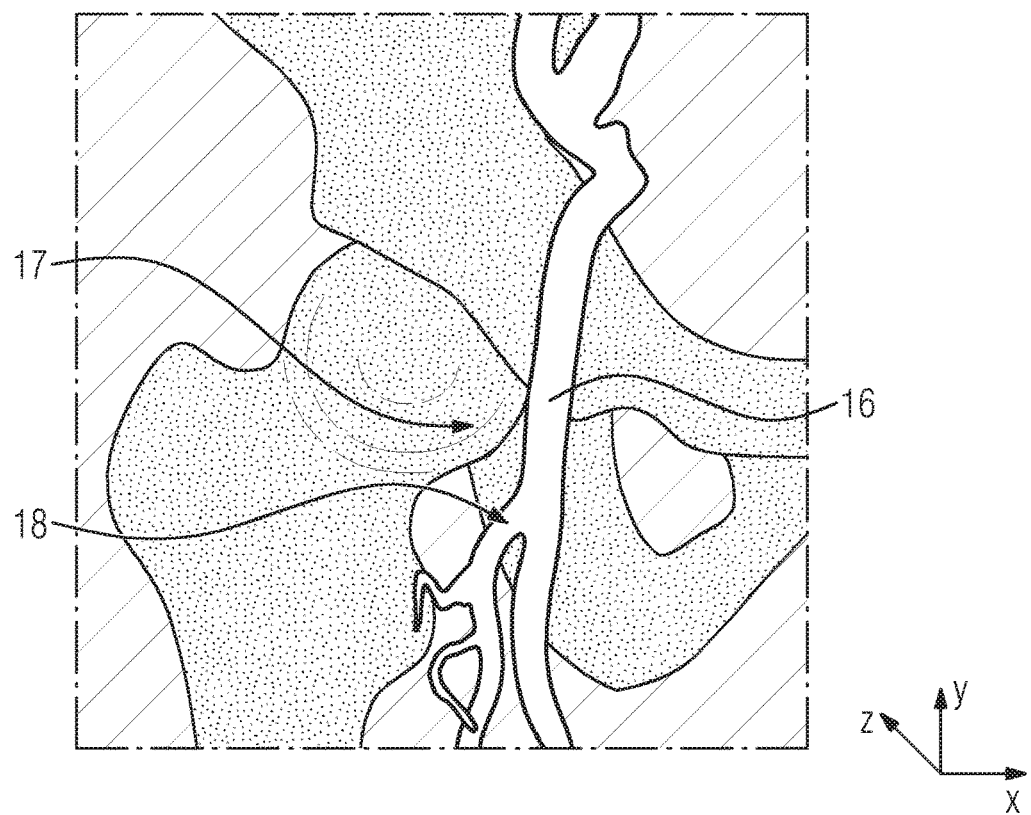
FIG. 2 shows an enlarged section of the schematic depiction of the pelvic region of the patient.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention generally relates to a method for the determination of a vessel puncture position comprising the reception of a first image dataset of a region of interest via an interface, wherein the first image dataset maps the vessel. The vessel in particular passes through the region of interest. A further step of the method according to at least one embodiment of the invention is the determination of a vessel line of the vessel based on the first image dataset via a computing unit. A further step of the method according to the invention is the determination of a gradient measure based on the vessel line. A further step of the method according to at least one embodiment of the invention is the determination of the vessel puncture position based on the gradient measure via the computing unit.

The inventors have recognized that catheters are usually introduced into vessels at a location that is as close as possible to the surface of the skin since this minimizes further tissue damage. Therefore, the determination based on the gradient measure of the vessel line enables the puncture position to be determined very precisely based on the first image dataset.

According to a further embodiment of the invention, the method includes the method step of the determination of a projected vessel line by projection of the vessel line along a first direction via the computing unit. Furthermore, the gradient measure is a gradient measure of the projected vessel line with respect to a second direction, wherein the second direction is orthogonal to the first direction. The first direction is in particular orthogonal to the sagittal plane of a patient, and the second direction is in particular orthogonal to the transverse plane of the patient. In other words, the first direction and the second direction in particular span the frontal plane of a patient. The inventors have recognized that a projected vessel line, in particular a two-dimensional projected vessel line, enables a gradient measure to be calculated in a particularly simple and efficient manner.

According to a further embodiment of the invention, the gradient measure is based on a tangent vector of the vessel line. The gradient measure can in particular also be based on a plurality of tangent vectors of the vessel line in a plurality of points of the vessel line. The inventors have recognized that the tangent vector of the vessel line enables the change therein, and hence in particular a gradient measure, to be determined particularly precisely.

According to a further possible embodiment, the vessel line of the vessel is determined based on segmentation of the vessel in the first image dataset. The inventors have recognized that the vessel line can be determined particularly precisely and efficiently based on an existing segmentation. This in particular also enables manual segmentations of the vessel in the first image dataset to be used as a starting point for the determination of the vessel line.

According to a further possible embodiment, the vessel line is determined as a basis for segmentation of the vessel in the first image dataset. In other words, therefore, first a vessel line is determined and segmentation of the vessel in the first image dataset could then be determined based on the vessel line. The inventors have recognized that a procedure of this kind does not require the segmentation of the vessel in the first image dataset to be determined and thus a procedure of this kind renders the performance of the method quicker and more cost-effective.

According to a further embodiment of the method, the determination of the puncture position is based on a zero point of the gradient measure. The inventors have recognized that the puncture position is in particular located close to a maximum or minimum of the vessel line, which are characterized by regions without any gradient or a gradient measure close to 0.

According to a further embodiment of the method, this furthermore includes the determination of a curvature measure based on the vessel line via the computing unit; the determination of the vessel puncture position is furthermore based on the curvature measure. The inventors have recognized that a curvature measure is particularly suitable for differentiating between a maximum and a minimum of the projected vessel line in order in this way to avoid errors in the determination of the puncture position.

According to a further possible embodiment of the invention, the determination of the puncture position is based on the plus-minus sign of the curvature measure. The inventors have recognized that using the plus-minus sign of the curvature measure as a basis enables differentiation between a maximum and a minimum of the projected vessel line to be performed particularly simply and therefore quickly.

According to a further possible embodiment of the invention, the curvature measure is a curvature measure of the projected vessel line with respect to the second direction. The inventors have recognized that a projected vessel line, in particular a two-dimensional projected vessel line, enables a curvature measure to be calculated particularly simply and efficiently.

According to a further possible embodiment of the invention, the curvature measure is based on a tangent vector of the vessel line. The curvature measure can in particular also be based on a plurality of tangent vectors of vessel line at several points of the vessel line. The inventors have recognized that using the basis of the tangent vector of the vessel line enables the change therein, and hence in particular a curvature measure, to be determined particularly precisely.

According to a further embodiment of the invention, the gradient measure is a first derivative and/or the curvature measure a second derivative. In particular when the gradient measure is a gradient measure of the projected vessel line, the gradient measure is a first derivative of the projected vessel line according to the second direction.

In particular when the curvature measure is a curvature measure of the projected vessel line, the curvature measure is a second derivative of the projected vessel line according to the second direction. In particular when the gradient measure is based on a tangent vector of the vessel line, the gradient measure is based on a first derivative according to the curve parameter. In particular when the curvature measure is based on a tangent vector of the vessel line, the curvature measure is based on a second derivative according to the curve parameter. A first and/or a second derivative can also be calculated based on only a part of the vessel line or the projected vessel line. The inventors have recognized that the first derivative is particularly suitable as a gradient measure and that the second derivative is particularly suitable as a curvature measure and that hence particularly precise determination of the puncture position is possible.

According to a further embodiment of the invention, the determination of the puncture position is furthermore based on an extremum of the vessel line, wherein the coordinates of the extremum differ from the coordinates of the puncture position. In other words, the extremum and the puncture position are two different points of the vessel line. The extremum is in particular an extremum of the projected vessel line. The inventors have recognized that using an extremum enables more precise and less error-susceptible determination of the puncture position since this extremum includes further information on the geometric route of the vessel line.

According to a further embodiment of the invention, the puncture position is situated distally or proximally to the extremum. The puncture position can in particular be situated distally to the extremum. The puncture position can in particular be situated proximally to the extremum. Herein, the puncture position is situated distally when it is situated in the route of the vessel further away from the center of the body or the heart than the extremum. Furthermore, herein the puncture position is situated proximally when it is situated in the route of the vessel nearer to the center of the body than the extremum. The inventors have recognized that, due to anatomical restrictions, only a smaller part of the projected vessel line has to be analyzed; as a result, on the one hand, the method is performed more quickly and, on the other, the method is less susceptible to errors.

According to a further possible embodiment of the invention, the vessel is an artery or a vein. The inventors have recognized that the method can be applied particularly efficiently for arteries and veins due to their geometry and their material properties.

According to a further embodiment of the invention, on the determination of vessel line, furthermore a first segmentation of the vessel is determined, furthermore the method includes the step of the reception of a second image dataset of the region of interest via the interface; the method furthermore includes the step of the determination of a second segmentation of the vessel based on the first segmentation, the puncture point of the vessel and the second image dataset via the computing unit. The inventors have recognized that the use of the puncture point enables the second segmentation to be determined more precisely and with less susceptibility to errors since the puncture point provides an additional fixed point for the adaptation of the segmentation.

According to a further embodiment of the invention, the second image dataset maps a medical instrument in the region of interest; the method furthermore includes the step of the determination of a first instrument position based on the second image dataset; the method furthermore includes the step of the extrapolation of a second instrument position based on the first instrument position and the puncture position; wherein the step of the determination of the second segmentation is performed such that the first instrument position and the second instrument position are arranged within the second segmentation of the vessel. A medical instrument is in particular an oblong instrument for examining a vessel. The medical instrument can in particular be a catheter; in this case, the first instrument position is a first catheter position and the second instrument position is a second catheter position. The inventors have recognized that an extrapolated instrument position enables the second segmentation to be determined particularly efficiently.

At least one embodiment of the invention also relates to a position-determining unit for the determination of a puncture position comprising:
an interface embodied to receive a first image dataset of a region of interest, wherein the first image dataset maps the vessel; and
a computing unit embodied to determine a vessel line of the vessel based on the first image dataset, determine a gradient measure based on the vessel line, and determine the vessel puncture position based on the gradient measure.

Such a position-determining unit can in particular be embodied to carry out the above-described methods according to at least one embodiment of the invention and the aspects thereof. The position-determining unit is embodied to carry out these methods and the aspects thereof in that the interface and the computing unit are embodied to carry out the corresponding method steps.

At least one embodiment of the invention furthermore relates to an imaging medical device comprising a position-determining unit according to at least one embodiment of the the invention. The imaging medical device is in particular embodied to record second image datasets. The imaging of the imaging medical device can in particular be based on ionizing radiation, in particular X-rays. The imaging medical device can in particular be a C-arm X-ray machine.

At least one embodiment of the invention also relates to a computer program product with a computer program and a computer-readable medium. A substantially software-based implementation has the advantage that it is also possible to retrofit position-determining units used to date in a simple way by way of a software update in order to operate in the manner according to at least one embodiment of the invention. In addition to the computer program, a computer program product of this kind can optionally include additional parts, such as, for example documentation and/or additional components and also hardware components, such as, for example, hardware keys (dongles etc.) for using the software.

An image dataset includes at least one image, furthermore an image dataset can also contain metadata. If the image is the result of an imaging medical examination, the metadata can in particular include the name, age and/or gender of the patient on whom the imaging medical examination was performed. A n-dimensional image dataset includes at least one n-dimensional image. An image dataset can in particular also be identical to an image, an n-dimensional image dataset can in particular be identical to a n-dimensional image. An image can in particular be the result of an imaging medical examination by way of ionizing radiation, in particular by way of X-rays. In this case, an (n-dimensional) image includes a set of (n-dimensional) voxels, wherein each of the voxels is assigned an intensity value based on an X-ray absorption coefficient. A two-dimensional voxel is also called a pixel.

The first image dataset is in particular a two-dimensional or a three-dimensional image dataset, the second image dataset is in particular a two-dimensional image dataset. The first image dataset can in particular have been determined with a first imaging medical device, the second image dataset can in particular have been determined with a second imaging medical device.

Segmentation is the term used for the creation of coherent structures in an image dataset by combining adjacent pixels or voxels that share a common property. Pixels or voxels which are parts of the image of the same body region are in particular assigned to a common coherent structure in the image dataset. Segmentation can be performed using known image-processing methods, such as edge-oriented methods, region-oriented methods, model-based methods or texture-oriented methods. Furthermore, segmentation of vascular structures can be preceded by the determination of one or more centerlines of vessels. The segmentation can then in particular be based on the centerlines determined.

Segmentation of a vessel in particular divides the first image dataset into a first region that corresponds to the vessel and a second region that does not correspond to the vessel. Herein, each voxel of the first image dataset can in particular be assigned a value, wherein the value is based on whether or not the associated voxel maps the vessel. For example, the voxels that map the vessel can be assigned the value 1 and the remaining voxels the value 0. If the first image dataset is a two-dimensional image dataset, the first and the second segmentation are in particular each two-dimensional segmentations. If the first image dataset is a three-dimensional image dataset, the first and the second segmentation are in particular each three-dimensional segmentations. Therefore, a segmentation can in particular also be understood as an image dataset with the same extension as the first image dataset. Herein, the second segmentation is in particular not segmentation of the second image dataset, but corresponds to the real vessel position during the examination with the medical instrument (which can differ from the vessel position in the first image dataset). Therefore, instead of "first segmentation" it is also possible to use "pre-calculated segmentation", instead of "second segmentation" it is therefore also possible to use "modified segmentation". Instead of the word "segmentation", it is also possible use the term "vascular structure".

A vessel line is in particular a set of points in the first image dataset, wherein each point of the set of points lies within the vessel. In other words, each point of the set of points is assigned to the vessel by segmentation of the vessel. Herein, the set of points can be discrete and continuous. If the vessel line is a discrete set of points, the vessel line can in particular be defined by the specification of the coordinates of all the points. In this case, a curve parameter can be defined by a sequence of the points, for example as an index. A point in the discrete set of points can correspond to a pixel or voxel but it can also be independent of a pixel or voxel in the first image dataset. If the vessel line is a continuous set of points, a vessel line can also be defined by a (optionally constant and/or differentiable) curve dependent on a (in particular continuous) curve parameter in the first image dataset. The vessel line can in particular also be the centerline of the vessel.

A projected vessel line is a projection of the vessel line with respect to a first direction. If the first image dataset is a two-dimensional image dataset, the projected vessel line is in particular identical to the vessel line. In other words, in this case, the first image dataset is extended in two directions, which are each orthogonal to the first direction, and the projection corresponds to identity mapping.

The puncture position is in particular defined by the specification of coordinates in the first image dataset. Consequently, a puncture position can also be identified by the specification of a point in a vessel line since a point in a vessel line can be assigned to coordinates in the three-dimensional image dataset. Alternatively, the puncture position can also be characterized by the specification of a voxel in the first image dataset.

An instrument position denotes a position of a part or a point of the medical instrument in particular in the first image dataset. If the first image dataset is a two-dimensional image dataset, the instrument position is in particular a two-dimensional position. If the first image dataset is a three-dimensional image dataset, the instrument position is in particular a three-dimensional instrument position. A first instrument position can in particular be determined based on the second image dataset. In particular when the medical instrument is a catheter, "catheter position" can be used synonymously with "instrument position".

The figures show the application of at least one embodiment of the invention to the vessel of the external iliac artery (the Latin technical term is "arteria iliaca externa") or its continuation, the femoral artery (the Latin technical term is "arteria femoralis"). Entry via these arteries can in particular be used for the treatment of an abdominal aortic aneurysm (AAA for short) by way of a stent graft (vascular prosthesis). However, at least one embodiment of the invention can also be applied to other vessels, for example the subclavian vein (the Latin technical term is "vena subclavia"), the subclavian artery (the Latin technical term is "arteria subclavia"), the cubital vein (the Latin technical term is "vena cubitalis"), the brachial artery (the Latin technical term is "arteria brachialis"), the radial artery (the Latin technical term is "arteria radialis") and the jugular vein (the Latin technical term is "vena jugularis"). Furthermore, at least one embodiment of the invention can also be used to calculate puncture points for peridural anesthesia or spinal anesthesia.

At least one embodiment of the invention can in particular be applied to other vessels because points of entry to vessels are advantageously selected close to the surface a patient in order, on the one hand, also actually to make contact with the vessel on the introduction of a medical instrument and, on the other, to minimize damage to the surrounding tissue as far as possible.

The advantageous embodiments, developments and features described in conjunction with the external iliac artery and the femoral artery can also be transferred to the application of at least one embodiment of the invention to other vessels.

Furthermore, the figures describe the invention with reference to the application of a catheter 36. The advantageous embodiments, developments and alternative features described can also be transferred to the application of another medical instrument, in particular a medical instrument with an oblong shape.

FIG. 1 shows a schematic depiction of the pelvic region of a patient 30, in particular the hip bones and arterial vessels, FIG. 2 shows an enlarged section of this depiction. FIG. 1 depicts the abdominal aorta 11 (the Latin technical term is "aorta abdominalis"), the two common iliac arteries 12 (the Latin technical term is "arteria iliaca communis", or in the plural "arteriae iliacae communes"), the two external iliac arteries 13 (the Latin technical term is "arteria iliaca externa", or in the plural "arteriae iliacae externae") and the two femoral arteries 14 (the Latin technical term is "arteria femoralis", or in the plural "arteriae femorales"). Also depicted are the two entry regions 15 in which the point of entry 16 of a catheter 36 to the femoral artery 14 is localized.

The point of entry 16 to the femoral artery 14 used is the point of the femoral artery 14 nearest to the surface, which is usually located about 2 to 5 cm below the skin of the patient 30. This point of entry 16 is easily localized by a palpable pulse and lies about 1 to 2 cm distal to the inguinal ligament (the Latin technical term is "ligamentum inguinale") next to the head 17 of the thigh bone (the Latin technical term is "caput ossis femoris"). FIG. 2 also depicts the bifurcation 18 of the femoral artery (or the branch of the deep femoral artery, in Latin "arteria profunda femoris") that lies distal to the point of entry 16.

Figure 3:
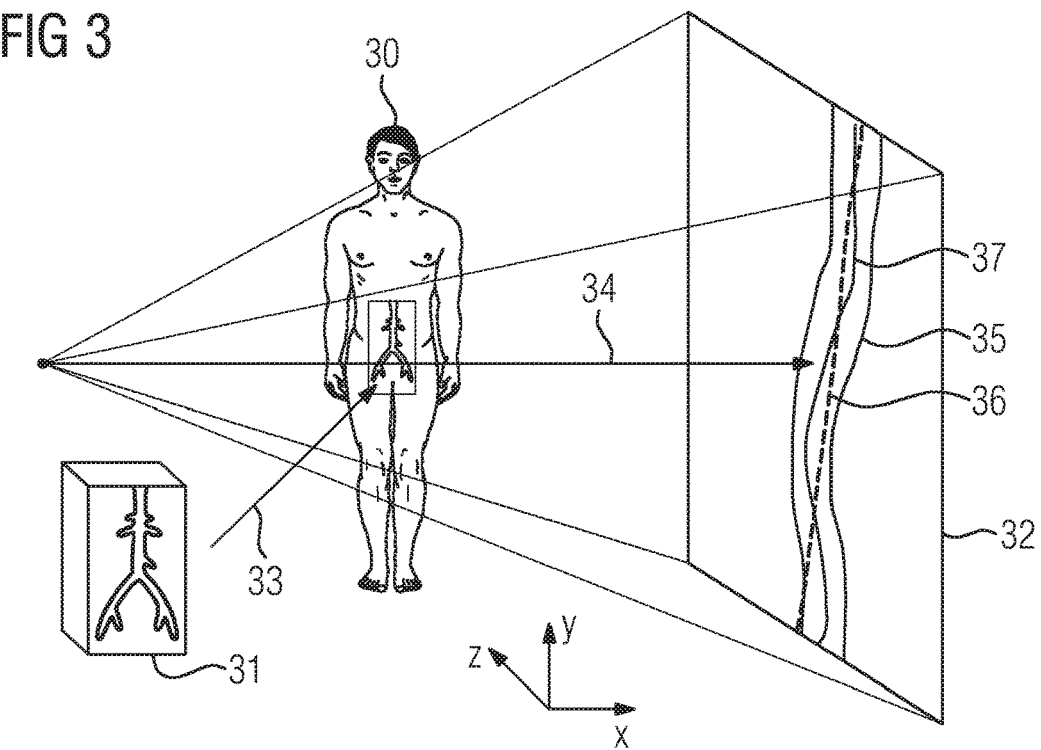
FIG. 3 shows the principle of the superimposition of a first image dataset and a second image dataset during catheterization.

FIG. 3 shows the principle of the superimposition of a first image dataset 31 and a second image dataset 32 during catheterization, wherein the first image dataset 31 was determined before catheterization, and wherein the second image dataset 32 was determined during catheterization. In the example embodiment depicted, the first image dataset 31 is a three-dimensional image dataset, which was determined by way of computed tomography. Alternatively, the first image dataset 31 can also be a three-dimensional image dataset determined, for example, by way of 3D rotational angiography. In the example embodiment depicted, the second image dataset 32 is furthermore a two-dimensional X-ray image dataset.

Herein, the first image dataset 31 is registered 33 with the patient 30 and can be depicted jointly with the second image dataset 32 by way of projection 34. In other words, the first image dataset 31 and the second image dataset 32 are registered with one another. Herein, in the example embodiment depicted, the projection of a first segmentation 35 of the first image dataset 31 is superimposed on the second image dataset 32. Herein, the second image dataset 32 also includes the image of the catheter 36. The projection of the first image dataset 31 and/or the projection of the first segmentation 35 of the first image dataset 31 can in particular also be called a "virtual image" or a "virtual X-ray image", the second image dataset can in particular also be called a "real image" or a "real X-ray image".

Figure 4:
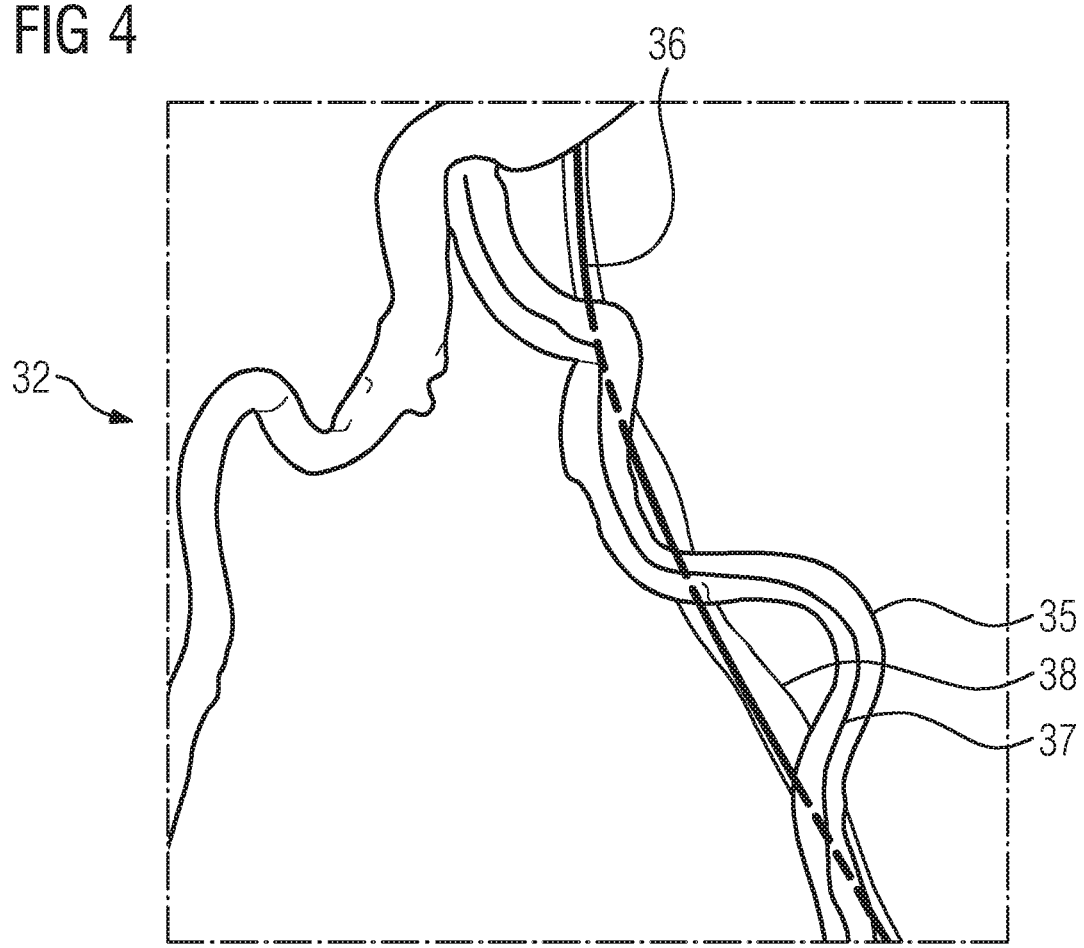
FIG. 4 shows a further superimposition of a first image dataset and a second image dataset during catheterization.

FIG. 4 shows a further superimposition of a first image dataset 31 and a second image dataset 32 during catheterization. The situation depicted shows a catheter 36 with high rigidity so that the vessel (here the common iliac arteries 12 and the external iliac artery 13) is deformed by the introduced catheter 36. As a result, the catheter 36 in the second image dataset 32 no longer extends through the projected first segmentation 35 (since the first segmentation 35 was determined based on the first image dataset 31, which was recorded before catheterization). In this situation, these deviations mean it is no longer possible to use the first image dataset 31 or the first segmentation 35 to assist catheterization. Furthermore, the second image dataset 32 depicts the image 38 of the vessel in which the catheter 36 extends.

Since it may be assumed that the vessel (here the common iliac arteries 12 and the external iliac artery 13) adapts itself to the shape of the catheter 36, the position of the catheter 36 in the second image dataset 32 due to deformation of the first segmentation 35 can be used as the basis for determining a second segmentation, which adapts the route of the vessel in the first image dataset 31 to the real circumstances.

Figure 5:
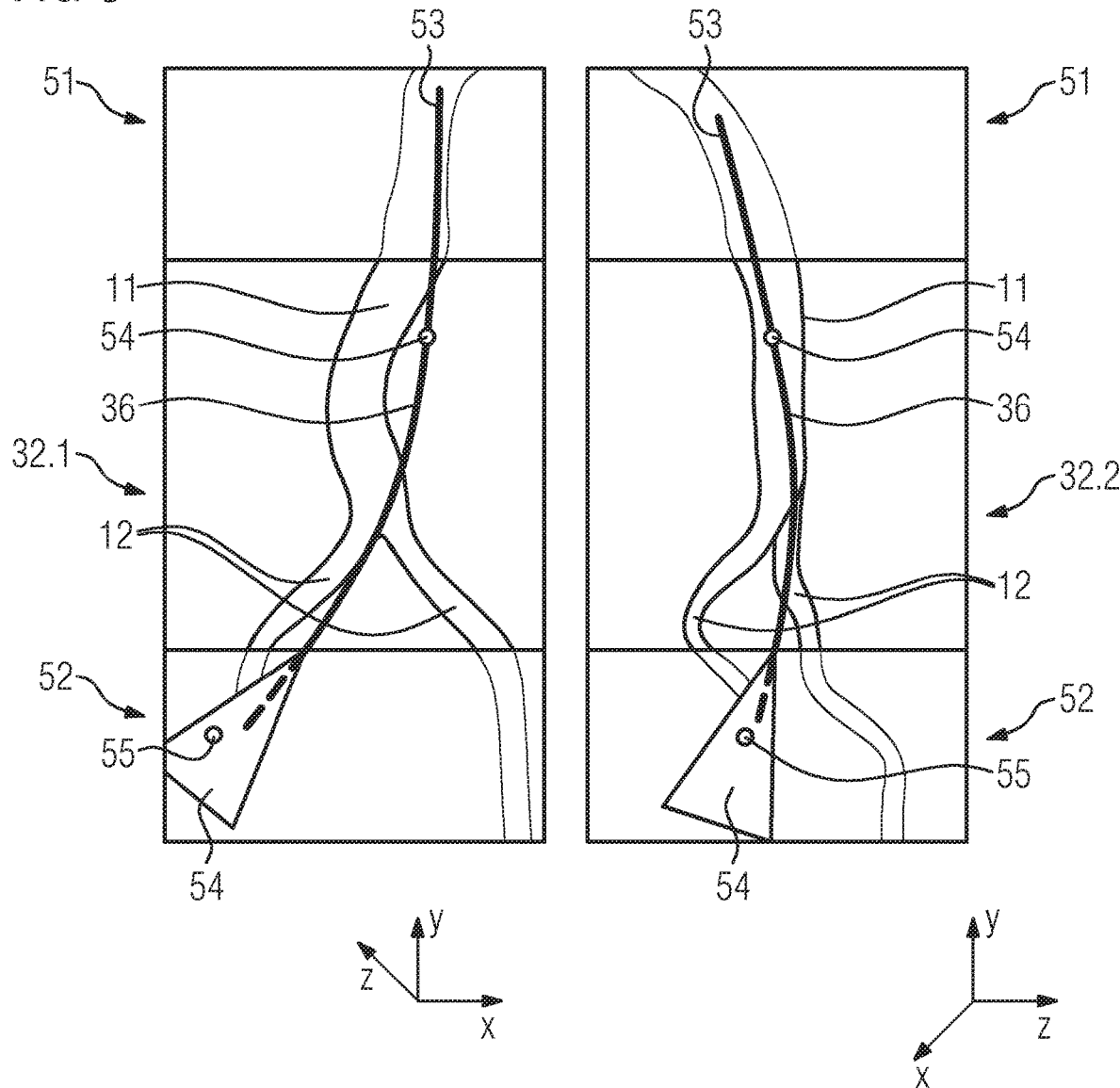
FIG. 5 shows a further superimposition of a first image dataset and a second image dataset during catheterization.

FIG. 5 shows a further superimposition of a first image dataset 31 and a second image dataset 32 during catheterization, which depicts an aortic bifurcation. In the example embodiment depicted, the second image dataset 32 includes a first two-dimensional image 32.1 and a second two-dimensional image of the region of interest, wherein the first two-dimensional image 32.1 and the second two-dimensional image 32.2 were recorded from different projection angles. To keep the X-ray dose for the patient 30 as low as possible, the field of view of the second image dataset 32 is kept as small as possible. Therefore, in particular the catheter 36 is not completely depicted in the second image dataset 32.

The example embodiment depicted contains a proximal region 51 and a distal region 52 in which the catheter 36 cannot be depicted, wherein, however, the proximal region 51 and the distal region 52 are depicted in the first image dataset 31. Since the rigidity of the vessels usually increases with an increasingly proximal location (i.e. closeness to the center of the body or to the heart), it can be assumed that the catheter 36 is unable to deform the vessel adequately in the proximal region 51 and, therefore, the proximal route 53 of the catheter 36 can be determined or approximated by the route of the vessel known from the first image dataset 31. However, this is not possible in the distal region 52 due to the lower rigidity of the vessel; in the distal region, the flexibility of the catheter 36 results in a region of uncertainty 54 for the route of the catheter 36. Determination of the puncture position in the distal region 52 causes a further point in the route of the catheter to be revealed and the region of uncertainty 54 can be reduced.

Furthermore, the depicted example embodiment depicts a first instrument position 54 and a second instrument position 55. Herein, the first instrument position 54 can be depicted in the second image dataset 32, the second instrument position 55 is not contained in the second image dataset 32 and lies in the distal uncertainty region 54 of the route of the catheter 36. Here, the first instrument position 54 and the second instrument position 55 are each three-dimensional instrument positions; in the two-dimensional second image dataset 32, it is in each case only possible to identify projections of the first instrument position 54 and the second instrument position 55. The determination of the first instrument position 54 and the second instrument position is illustrated in more detail in FIG. 9 and the associated description.

Figure 6:
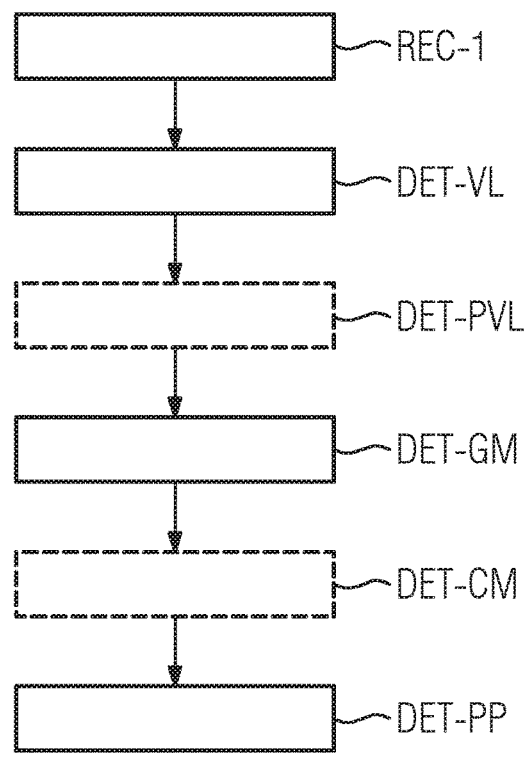
FIG. 6 shows a flow diagram of a first example embodiment of the method according to an embodiment of the invention for the determination of a puncture position.

FIG. 6 shows a flow diagram of a first example embodiment of the method according to the invention for the determination of a puncture position.

The first step of the example embodiment depicted is the reception REC-1 of a first image dataset 31 of a region of interest via an interface 91, wherein the first image dataset 31 maps the vessel. In the example embodiment depicted, the first image dataset 31 is a three-dimensional image dataset, and the first image dataset 31 includes the abdominal aorta 11 of a patient 30 and the two common iliac arteries 12 of the patient 30. Furthermore, the three-dimensional first image dataset 31 also includes one or both external iliac arteries 13 and one or both femoral arteries 14 of the patient 30.

The second step of the example embodiment depicted is the determination DET-VL of a vessel line 37 of the vessel based on the first image dataset 31 via a computing unit 92. Herein, methods for the determination of the vessel line 37 are known to the person skilled in the art, for example from the publication V. R. Goel et al., "Automated Vascular Geometric Analysis of Aortic Aneurysms", IEEE Comput. Graph Appl. 2008, 28(3), pages 76-86, the entire contents of which are hereby incorporated herein by reference.

The third step of the example embodiment depicted is the determination DET-PVL of a projected vessel line 71 by projection 34 of the vessel line 37 along a first direction x via the computing unit 92. This projected vessel line 71 is used to determine a gradient measure 72 based on the vessel line 37. In the example embodiment depicted, the vessel line 37 is defined by a set of three-dimensional voxels in the first image dataset 31, wherein each of the voxels has a coordinate with respect to the first direction x, a second direction y and a third direction z. The vessel line 71 projected with respect to the first direction is then defined by a set of pixels which result from the omission of the coordinates of the vessel line points with respect to the first direction x and now only have a coordinate with respect to the second direction y and a coordinate with respect to the third direction. If the first direction x does not correspond to one of the coordinate axes, a general projection operator can be applied to the coordinates of the points. The projected vessel line 71 can then also be generally transferred into an implicit discrete form $z(y)$. It is then also optionally and advantageously possible to interpolate the pixels of the projected vessel line 71 in order to arrive at a continuous projected vessel line 71 or at a differentiable projected vessel line 71.

Alternatively, the vessel line 37 can also be defined by a curve in three-dimensional space, i.e. by a function $\mathbb{R} \to \mathbb{R}^3$, $s \to (x(s), y(s), z(s))$ that maps a curve parameter s on a three-dimensional coordinate. The projected vessel line 71 is then defined by a curve in two-dimensional space produced by the application of a projection operator to the three-dimensional curve, for example by the function $\mathbb{R} \to \mathbb{R}^2$, $s \to (y(s), z(s))$. This projected vessel line 71 can then be generally transferred to an implicit form z(y). Naturally, projection in any direction desired is also possible by the choice of any projection operator.

The determination DET-PVL of the projected vessel line 71 is an optional step. This step can in particular be omitted if the gradient measure 72 and the curvature measure 73 are to be calculated not on the basis of the projected vessel line 71 but in each case on the basis of a tangent vector of the vessel line 37.

The fourth step of the example embodiment depicted is the determination DET-GM of a gradient measure 72 of the projected vessel line 71 with respect to a second direction y via the computing unit 92, wherein the second direction y is orthogonal to the first direction x.

In the example embodiment depicted, the gradient measure 72 used is a discrete first derivative (another technical term is difference quotient) of the projected vessel line 71

$$z'_d(y) = \frac{z(y+h) - z(y)}{h}$$

wherein the pixel spacing h is usually selected as h=1. In particular when the projected vessel line 71 is a smooth function, the continuous first derivative (another technical term is differential quotient) z'(y) can also be used as the gradient measure 72. Optionally, a discrete first derivative can be smoothed by filtering in order to reduce the influence of noise. This gradient measure 72 is a gradient measure 72 with respect to the second direction y. Therefore, the gradient measure 72 is in particular based on the vessel line 37.

Alternatively, a gradient measure 72 can also be determined based on a tangent vector of the vessel line 37. If the vessel line 37 is defined by a set of points $p_1, \ldots, p_N$, then, in a point $p_i$, the tangent vector $t_i$ corresponds to a difference vector of two points of the vessel line 37, for example $t_i = (p_{i+1} - p_i)/|p_{i+1} - p_i|$ or $t_i = (p_{i+1} - p_{i-1})/|p_{i+1} - p_{i-1}|$, wherein $|p_i - p_j|$ is the Euclidean distance between the points $p_i$ and $p_j$. This can be understood as a discrete first derivative with respect to the curve parameter, which is used here as an index. If the vessel line 37 is defined by a differentiable curve $g(s) = (x(s), y(s), z(s))$, the tangent vector $t(s_0)$ can be defined in a point $g(s_0)$, for example using the component-wise derivative according to the curve parameter s:

$$t(s_0) = \left( \frac{dx(s)}{ds}\bigg|_{s_0}, \frac{dy(s)}{ds}\bigg|_{s_0}, \frac{dz(s)}{ds}\bigg|_{s_0} \right)$$

The tangent vector can be used as the basis for the calculation of a scalar gradient measure 72 in a point by scalar multiplication of the tangent vectors by a unit vector, wherein the unit vector points in the prespecified direction. For example, a gradient measure 72 can be defined by $t_i \circ e_3$ or $t(s) \circ e_3$, wherein $e_2 = (0, 0, 3)$ is a unit vector in the third direction z.

A fifth and optional step of the example embodiment depicted is the determination DET-CM of a curvature measure 73 of the projected vessel line 71 with respect to the second direction y via the computing unit 92. Therefore, the curvature measure 73 is in particular based on the vessel line 37.

In the example embodiment depicted, a discrete second derivative of the projected vessel line 71 is used as the curvature measure 73:

$$z''_d(y) = \frac{z(y+h) - 2z(y) + z(y-h)}{h^2}$$

wherein the pixel pitch h is usually selected as h=1. In particular when the projected vessel line 71 is a smooth function, the continuous second derivative (another term is differential quotient) z''(y) can also be used as the curvature measure 73. Optionally, a discrete second derivative can be smoothed by filtering in order to reduce the influence of noise. This curvature measure 73 is a curvature measure 73 with respect to the second direction y.

Alternatively, a curvature measure 73 can also be determined based on a tangent vector of the vessel line 37, in particular on a difference of two tangent vectors and/or in particular based on a curvature vector. If the vessel line 37 is defined by a set of points $p_1, \ldots, p_N$, a curvature measure 73 can be determined by scalar multiplication of a unit vector by a curvature vector $k_i = (t_{i+1} - t_i)/|p_{i+1} - p_i|$ or $k_i = (tp_{i+1} - t_{i-1})/|p_{i+1} - p_{i-1}|$. This can be understood as a discrete second derivative with respect to the curve parameter, which is used here as an index. If the vessel line 37 is defined by a differentiable curve $g(s) = (x(s), y(s), z(s))$, the curvature vector $k(s_0)$ can be defined in a point $g(so)$ for example using the component-wise second derivative according to the curve parameter s:

$$k(s_0) = \left( \frac{d^2 x(s)}{ds^2}\bigg|_{s_0}, \frac{d^2 y(s)}{ds^2}\bigg|_{s_0}, \frac{d^2 z(s)}{ds^2}\bigg|_{s_0} \right)$$

The curvature vector k is in particular the component-wise first derivative of the tangent vector t according to the curve parameter s, i.e. the curvature vector k is also based on the tangent vector t of the vessel line 37. The curvature vector can be used as the basis for the calculation of a scalar curvature measure 73 in a point by scalar multiplication of the curvature vector by a unit vector. For example, a curvature measure 73 can be defined by $k_i \circ e_3$ or $k(s) \circ e_3$, wherein $e_3 = (0, 0, 1)$ is a unit vector in the third direction z.

The sixth step of the example embodiment depicted is the determination DET-PP of the puncture position 74 of the vessel based on the gradient measure 72 and the curvature measure 73 via the computing unit 92. Alternatively, the determination DET-PP of the puncture position 74 can also be based only on the curvature measure 73. Further alternatively, the determination DET-PP of the puncture position 74 can additionally be based on a further extremum of the vessel line 37 and/or the projected vessel line 71. The determination DET-PP of the puncture position 74 is depicted in detail in FIG. 7 and the associated description.

Figure 7:
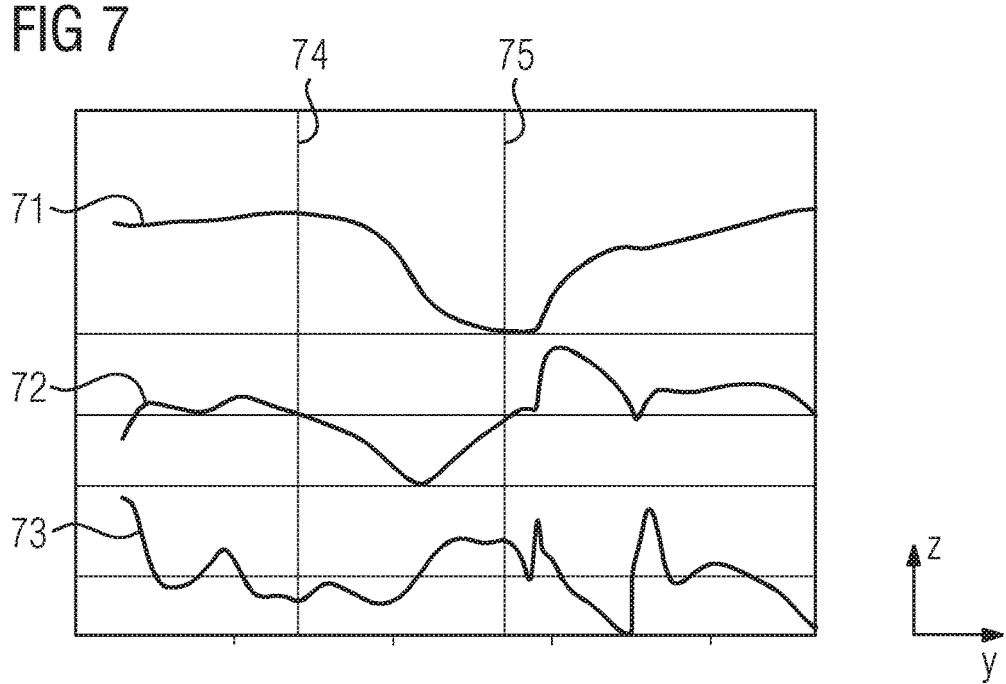
FIG. 7 shows a projected vessel line, a gradient measure and a curvature measure.

FIG. 7 shows a projected vessel line 71, a gradient measure 72 and a curvature measure 73. The gradient measure 72 is a discrete first derivative of the projected vessel line 71 with respect to the second direction y, the curvature measure 73 is a discrete second derivative of the projected vessel line 71 with respect to the second direction. However, the procedure described here can also be used in a similar way when the gradient measure 72 and/or the curvature measure 73 are based on a tangent vector of the vessel line 37.

FIG. 7 also depicts an extremum 75, which is the global minimum of the projected vessel line 71. This global minimum can be determined solely on the basis of the gradient measure 72 in that the value of the projected vessel line 71 is determined for all zero points of the gradient measure 72 (wherein, here, the value corresponds to the coordinate with respect to the third direction z), and the zero point with the smallest corresponding value of the projected vessel line 71 is used as the extremum 75 or global minimum. It is also possible to use the plus-minus sign of the curvature measure 73 to differentiate between a minimum and a maximum of the projected vessel line 71.

The extremum 75 can then be used to determine the puncture point 74 in a simpler way, in this case the puncture point 74 is the maximum distal to the extremum 75, which has the shortest distance from the extremum 75 with respect to the second coordinate y. Alternatively, the puncture position 71 can also be determined as the global maximum distal to the extremum 75; as another alternative, the puncture position 74 can also be determined as the global maximum of the projected vessel line 71.

Figure 8:
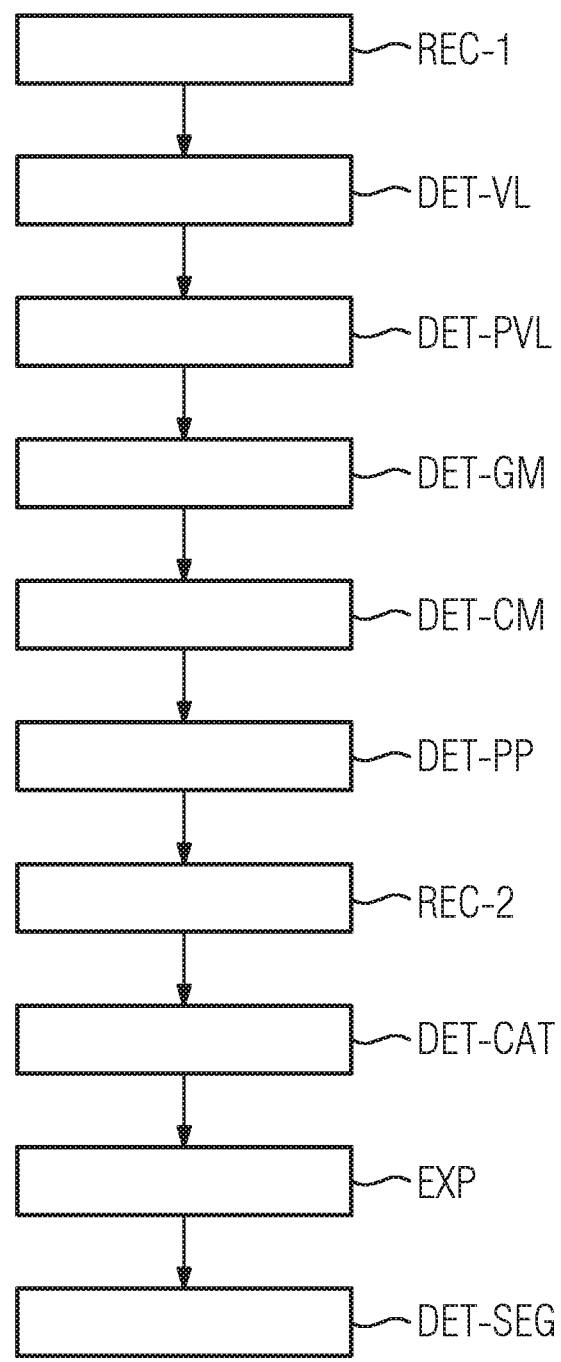
FIG. 8 shows a flow diagram of a second example embodiment of the method according to the invention for the determination of a puncture position.

FIG. 8 shows a second example embodiment of the method for the determination of a puncture position 74. The steps of the reception REC-1 of a first image dataset 31, the determination DET-VL of a vessel line 37, the determination DET-PVL of a projected vessel line 71, the determination DET-GM of a gradient measure 72, the determination DET-GM of a curvature measure 73 and the determination DET-PP of the puncture position 74 are identical to the example embodiment in FIG. 6. The steps named can in particular comprise the advantageous embodiments and developments named in the description for FIG. 6.

The seventh step of the example embodiment depicted is the reception REC-2D of a second image dataset 32 of the region of interest via the interface 91, wherein the second image dataset 32 depicts a catheter 36 in the region of interest. In this example embodiment, the second image dataset 32 is a two-dimensional image dataset, which was recorded via a second imaging medical device 96. For example, the second image dataset 32 can be the image dataset depicted in FIG. 5. The second image dataset 32 is in particular recorded during catheterization, in other words at a time at which a catheter 36 is introduced into the vessel.

The eighth step of the example embodiment depicted is the determination DET-CAT of a first instrument position 54 based on the second image dataset 32. In the example embodiment depicted, the first instrument position 54 is a three-dimensional position, which is in particular defined by the specification in each case of a coordinate with respect to the first direction x, the second direction y and the third direction z. If, as in the example embodiment depicted, the second image dataset 32 is a two-dimensional image dataset, this can include at least two two-dimensional images, wherein these two two-dimensional images were recorded from different directions in order to reconstruct a three-dimensional position from the at least two two-dimensional coordinates. Alternatively, it known from publication US 20150094567 A1, the entire contents of which are hereby incorporated herein by reference, to determine the first instrument position based on only a two-dimensional image. If, alternatively, the second image dataset 32 is a three-dimensional image dataset, the coordinates of the first instrument position 54 can be read directly from the second image dataset 32.

Alternatively, the first instrument position 54 can also be a two-dimensional position, which is in particular defined by the specification in each case of a coordinate with respect to the second direction y and the third direction z. If the second image dataset 32 is then a two-dimensional image dataset, the first instrument position 54 can be read directly from the second image dataset 32. Alternatively, if the second image dataset 32 is a three-dimensional image dataset, the two-dimensional first instrument position 54 can be determined by projection of a directly readable three-dimensional instrument position, in particular by projection with respect to the first direction x.

The ninth step of the example embodiment depicted is the extrapolation EXP of a second instrument position 55 based on the first instrument position 54 and the puncture position 74. To this end, in this example embodiment, a curve is determined by the first instrument position 54 and the puncture position 74 (by determining the parameters of the polynomial), which approximates the route of the vessel. The second instrument position 55 is then a point of this curve between the first instrument position 54 and the puncture position 74. Herein, the curve can be selected as a straight line through the first instrument position and the puncture position 74; alternatively, assuming curvature of the vessel, it is also possible for other curves, such as, for example, higher-grade polynomials, splines or NURBS ("non-uniform rational B-splines") to be selected by the first instrument position 54 and the puncture position 74.

Advantageously, it is also possible to use a plurality of first instrument positions 54 to determine a second instrument position 55. If the equation system is overdetermined for the determination of the parameters of the curve, these can be determined can by regression calculus (the English technical term is "fitting"), for example based on the least squares method. Advantageously, the second instrument position 55 can also be based on one or more first instrument directions, for example on the tangent vector of the catheter 36 in the one or the more first instrument position 54.

The tenth step of the example embodiment depicted is the determination DET-SEG of a second segmentation of the vessel based on the first segmentation 35, the puncture position 74 of the vessel and the second image dataset 32 via the computing unit 92. Herein, the determination (ET-SEG) of the second segmentation is performed such that the first instrument position 54 and the second instrument position 55 are arranged within the second segmentation of the vessel.

Figure 9:
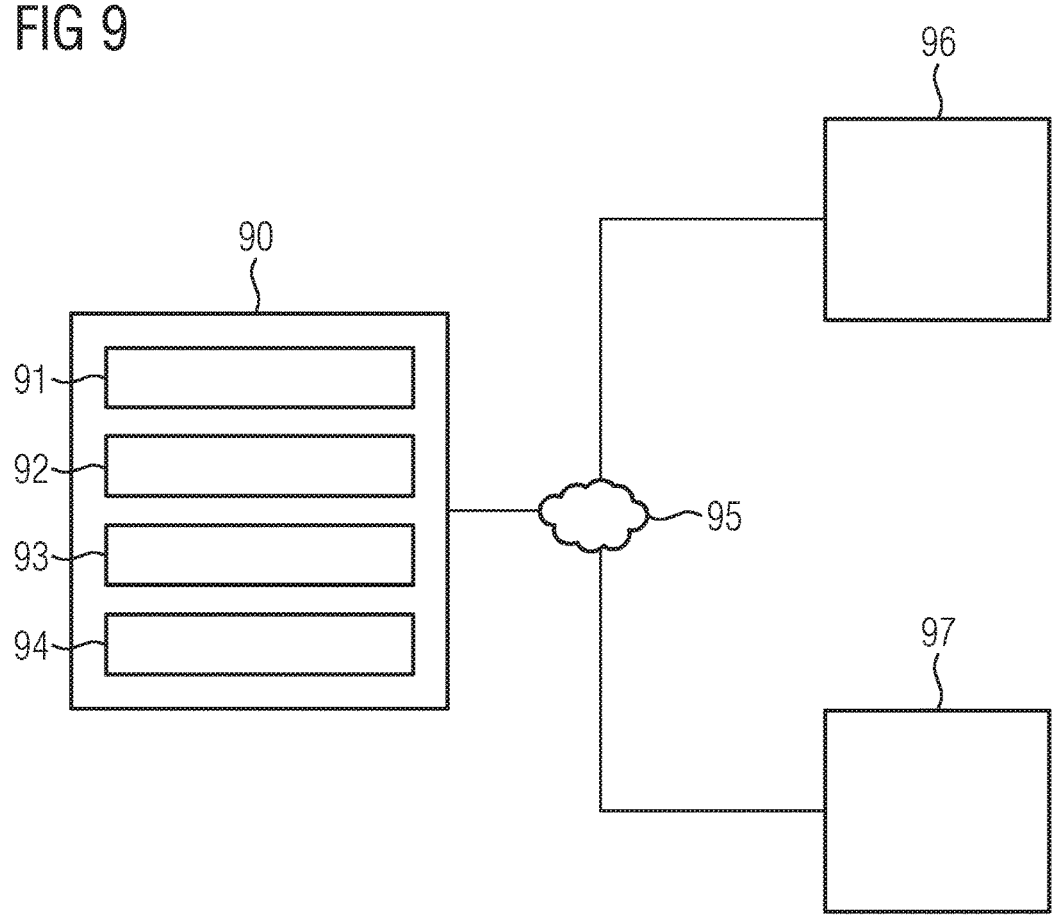
FIG. 9 shows a position-determining unit 90 for the determination of a puncture position.
Figure 10:
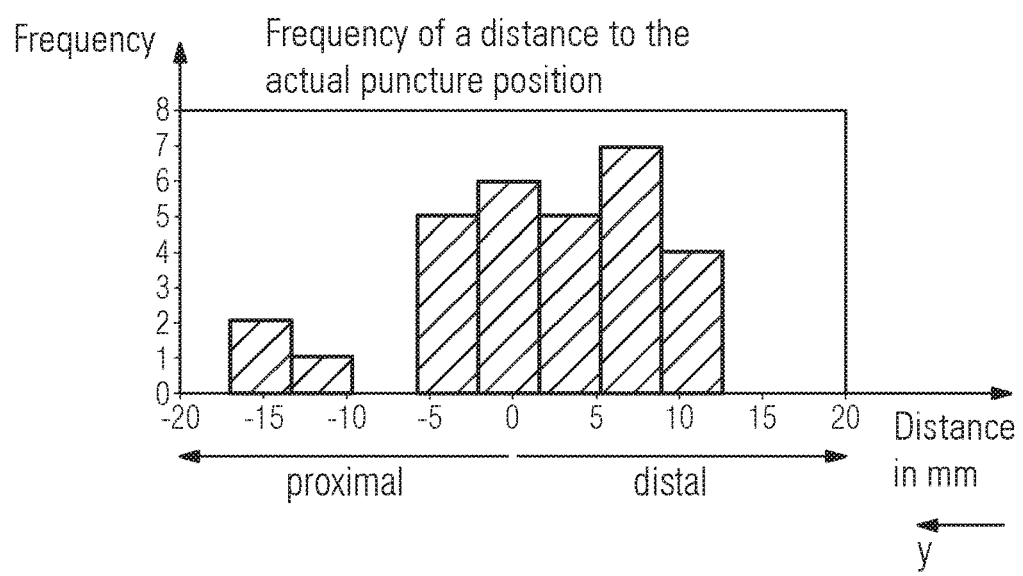
FIG. 10 shows experimental data produced by the use of the depicted method for the determination of a puncture position.

FIG. 9 shows a position-determining unit 90 for the determination of a puncture position. The position-determining unit 90 shown here is designed to carry out a method according to the invention. This position-determining unit 90 includes an interface 91, a computing unit 92, a memory unit 93 and an input/output unit 94.

The position-determining unit 90 can in particular be a computer, a workstation, a microcontroller or an integrated circuit. Alternatively, the position-determining unit 90 can be a real or virtual group of computers (an English technical term for a real group is "cluster", an English technical term for a virtual group is "cloud").

An interface 91 can be a hardware or software interface (for example PCI-Bus, USB or Firewire). A computing unit 92 can comprise hardware elements or software elements, for example a microprocessor or a so-called FPGA (English abbreviation for "field programmable gate array"). A memory unit 93 can be implemented as a non-permanent working memory (random access memory, RAM) or as a permanent mass storage (hard disk, USB stick, SD card, solid state disk). An input/output unit 94 includes at least one input unit and/or at least one output unit.

In this example embodiment, the position-determining unit 90 is connected via a network 94 to a first imaging medical device 95 and a second imaging medical device 96. The network 94 can be a local area network ("LAN" for short) or a "wide area network" ("WAN" for short). An example of a local area network is an intranet, an example of a wide-area network is the internet. The network 94 can in particular also be wireless, in particular a WLAN ("wireless LAN", the abbreviation "WiFi" is commonly used in English) or as a Bluetooth connection. The network 94 can also be embodied as a combination of these examples.

Alternatively, it is also possible for the position-determining unit 90 to be connected via a first network to the first imaging medical device 95 and via a second network to the second imaging medical device 96, wherein the first and the second network can comprise the embodiments and developments of the network 94. Alternatively, it is also possible for the position-determining unit 90 to be embodied as part of the first imaging device 95 and for the first imaging device 95 to be connected to the second imaging device 96 (optionally via a network). Alternatively, it is also possible for the position-determining unit 90 to be embodied as part of the second imaging device 96 and for the second imaging device 96 to be connected to the first imaging device 95 (optionally via a network). For the purposes of this explanation, a connection (optionally via a network) also exists if the first or the second imaging medical device 95, 96 stores the first image dataset 31 or the second image dataset 32 in a central memory unit and the position-determining unit 90 accesses this central memory unit. This central memory unit can in particular be a PACS (English: "picture archiving and communication system"), a RIS (English: "radiology information system") or a HIS (English "hospital information system"). In all the alternatives depicted, it is also possible for there to be a connection to only one of the two imaging modalities 95, 96.

The first imaging medical device 95 is embodied to record a first image dataset 31. If the first image dataset 31 is a three-dimensional image dataset, the first imaging medical device can in particular be a computed tomography scanner, a magnetic resonance device or a C-arm X-ray machine, wherein the C-arm X-ray machine is embodied to record two-dimensional X-ray images from several directions and reconstruct them as a three-dimensional image dataset. If the first image dataset 31 is a two-dimensional image dataset, the first imaging medical device 95 can be an X-ray fluoroscopy machine, in particular a C-arm X-ray machine. During the recording of the first image dataset 31 with the first imaging medical device 95, it is in particular possible to use an X-ray contrast medium when the recording is performed using X-rays.

The second imaging medical device 95 is embodied to record a second image dataset 32. The second imaging medical device 96 can in particular be an X-ray fluoroscopy machine, in particular a C-arm X-ray machine. During the recording of the second image dataset 32 with the second imaging medical device 96, it is in particular possible to use an X-ray contrast medium when the recording is performed using X-rays.

FIG. 11 shows experimental data resulting from use of the depicted method for the determination of a puncture position. Herein, the puncture position was determined based on fifteen bilateral (i.e. thirty in total) three-dimensional image datasets from fifteen patients with the method according to the invention, wherein each of the three-dimensional image datasets is a computed tomography scan. As a comparison, for each of the three-dimensional image datasets, a reference position was ascertained by way of manual annotation of the three-dimensional image dataset by a radiologist. The histogram plots the relative frequency of the deviations between the puncture position determined by the method and the reference position. The mean value of the deviation is 6.3 mm±4.5 mm; in 24 of the 30 datasets, the deviation is less than 10 mm. The maximum deviation is 18 mm. Accuracy can be assessed with reference to the diameter of a catheter 36 for the treatment of an abdominal aortic aneurysm, which is 7 mm.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a vessel puncture position of a vessel, comprising:
   receiving, via an interface, a first image dataset of a region of interest, the first image dataset mapping the vessel;
   determining, via at least one processor, a vessel line of the vessel based on the first image dataset received;
   determining, via the at least one processor, a gradient measure of the vessel line determined; and
   determining, via the at least one processor, the vessel puncture position of the vessel based on the gradient measure determined, wherein the puncture position designates a point in the first image dataset describing a probable location at which a catheter penetrates the vessel.

2. The method of claim 1, comprising:
   determining, via at least one processor, a projected vessel line of the vessel by projection of the vessel line along a first direction, wherein the gradient measure is a gradient measure based upon the projected vessel line determined, with respect to a second direction, the second direction being orthogonal to the first direction.

3. The method of claim 2, wherein the gradient measure is based on a tangent vector of the vessel line.

4. The method of claim 2, wherein the vessel puncture position is determined based on a zero point of the gradient measure.

5. The method of claim 2, further comprising:
   determining, via the at least one processor, a curvature measure based on the vessel line determined, wherein the determining of the vessel puncture position of the vessel is also based on the curvature measure.

6. The method of claim 2, wherein the determining of the vessel puncture position is further based on an extremum of the vessel line, and wherein coordinates of the extremum differ from coordinates of the vessel puncture position.

7. The method of claim 6, wherein the vessel puncture position is situated distally or proximally with respect to the extremum.

8. The method of claim 2, wherein, in the determining of the vessel line, a first segmentation of the vessel is determined, the method further comprising:
   receiving, via the interface, a second image dataset of the region of interest; and
   determining, via the at least one processor, a second segmentation of the vessel based on the first segmentation, the vessel puncture position and the second image dataset.

9. The method of claim 8, wherein the second image dataset maps a medical instrument in the region of interest, the method further comprising:
   determining, via the at least one processor, a first instrument position based on the second image dataset; and
   extrapolating, via the at least one processor, a second instrument position based on the first instrument position and the vessel puncture position, wherein the determining of the second segmentation is performed such that the first instrument position and the second instrument position are arranged within the second segmentation of the vessel.

10. A non-transitory computer program product storing a computer program, directly loadable into a memory of a position-determining unit, the computer program including program sections for executing the method of claim 2 when the program sections are executed by the position-determining unit.

11. A non-transitory computer-readable storage medium storing program sections, readable and executable by a position-determining unit, to carry out the method of claim 2 when the program sections are executed by the position-determining unit.

12. The method of claim 1, wherein the gradient measure is based on a tangent vector of the vessel line.

13. The method of claim 1, wherein the vessel puncture position is determined based on a zero point of the gradient measure.

14. The method of claim 1, further comprising:
   determining, via the at least one processor, a curvature measure based on the vessel line determined, wherein the determining of the vessel puncture position of the vessel is also based on the curvature measure.

15. The method of claim 14, wherein the curvature measure is a second derivative.

16. The method of claim 14, wherein at least one of
   the gradient measure is a first order derivative; and
   the curvature measure is a second order derivative.

17. The method of claim 1, wherein the determining of the vessel puncture position is further based on an extremum of the vessel line, and wherein coordinates of the extremum differ from coordinates of the vessel puncture position.

18. The method of claim 17, wherein the vessel puncture position is situated distally or proximally with respect to the extremum.

19. The method of claim 1, wherein, in the determining of the vessel line, a first segmentation of the vessel is determined, the method further comprising:
   receiving, via the interface, a second image dataset of the region of interest; and
   determining, via the at least one processor, a second segmentation of the vessel based on the first segmentation, the vessel puncture position and the second image dataset.

20. The method of claim 19, wherein the second image dataset maps a medical instrument in the region of interest, the method further comprising:
   determining, via the at least one processor, a first instrument position based on the second image dataset; and
   extrapolating, via the at least one processor, a second instrument position based on the first instrument position and the vessel puncture position, wherein the determining of the second segmentation is performed such that the first instrument position and the second instrument position are arranged within the second segmentation of the vessel.

21. The method of claim 1, wherein the gradient measure is a first derivative.

22. A non-transitory computer program product storing a computer program, directly loadable into a memory of a position-determining unit, the computer program including program sections for executing the method of claim 1 when the program sections are executed by the position-determining unit.

23. A non-transitory computer-readable storage medium storing program sections, readable and executable by a position-determining unit, to carry out the method of claim 1 when the program sections are executed by the position-determining unit.

24. A position-determining unit for determining a puncture position of a vessel, comprising:
   interface, embodied to receive a first image dataset of a region of interest, the first image dataset mapping the vessel; and
   at least one processor, embodied to
      determine a vessel line of the vessel based on the first image dataset received,
      determine a gradient measure of the vessel line determined, and
      determine the puncture position based on the gradient measure determined, wherein the puncture position designates a point in the first image dataset describing a probably location at which a catheter penetrates the vessel.

25. An imaging medical device comprising the position-determining unit of claim 24.

26. A position-determining unit for determining a puncture position of a vessel, comprising:
- interface, embodied to receive a first image dataset of a region of interest, the first image dataset mapping the vessel; and
- at least one processor, embodied to
    - determine a projected vessel line of the vessel by projection of a vessel line along a first direction, the vessel line being based on the first image dataset received,
    - determine a gradient measure of the projected vessel line determined, with respect to a second direction, the second direction being orthogonal to the first direction, and
    - determine the puncture position based on the gradient measure determined, wherein the puncture position designates a point in the first image dataset describing a probably location at which a catheter penetrates the vessel.

27. An imaging medical device comprising the position-determining unit of claim 26.

* * * * *